United States Patent
Bosio et al.

(10) Patent No.: US 9,080,149 B2
(45) Date of Patent: Jul. 14, 2015

(54) SEPARATION OF LIVING UNTOUCHED NEURONS

(71) Applicant: Miltenyi Biotec GmbH, Bergisch Gladbach (DE)

(72) Inventors: Andreas Bosio, Cologne (DE); Melanie Jungblut, Cologne (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 0 days.

(21) Appl. No.: 13/779,660

(22) Filed: Feb. 27, 2013

(65) Prior Publication Data
US 2013/0316373 A1 Nov. 28, 2013

(30) Foreign Application Priority Data
Mar. 1, 2012 (EP) .................................. EP12157671

(51) Int. Cl.
*G01N 33/569* (2006.01)
*C12N 5/079* (2010.01)
*C07K 16/28* (2006.01)
*C12N 5/0793* (2010.01)

(52) U.S. Cl.
CPC .......... *C12N 5/0619* (2013.01); *C07K 16/2848* (2013.01); *C12N 5/0622* (2013.01); *G01N 33/56966* (2013.01)

(58) Field of Classification Search
CPC ............. C07K 16/2848; C12N 5/0619; C12N 5/0622; G01N 33/56966
See application file for complete search history.

(56) References Cited

U.S. PATENT DOCUMENTS

| | | | |
|---|---|---|---|
| 5,411,863 A | 5/1995 | Miltenyi | |
| 5,543,289 A | 8/1996 | Miltenyi | |
| 6,020,210 A | 2/2000 | Miltenyi | |
| 6,417,011 B1 | 7/2002 | Miltenyi | |
| 2011/0123550 A1* | 5/2011 | Shibayama et al. | 424/172.1 |

FOREIGN PATENT DOCUMENTS

| | | |
|---|---|---|
| WO | WO-2005/121318 A2 | 12/2005 |
| WO | WO-2005/121318 A3 | 12/2005 |

OTHER PUBLICATIONS

Anton et al. 1999 "distinct functions of alpha3 and alphaV integrin receptors in neuronal migration and laminar organization of the cerebral cortex" Neuron 22:277-289.*
Azari et al. 2011 "purification of immature neuronal cells from neural stem cell progeny" PLOS One 6(6):e20941-e20941.*
Cahoy et al. 2008 "A transcriptome database for astrocytes, neurons, and oligodendrocytes: a new resource for understanding brain development and function" J Neurosci 28(1):264-278.*
Miltenyibiotec "Neuron Isolation Kit, Mouse" accessed from http://www.miltenyibiotec.com on Dec. 10, 2013.*
MACS Miltenyi Biotec 2011 "Neuroscience: Inspiring technology for creative scientists" accessed from https://www.miltenyibiotec.com/~/media/Files/Navigation/Cell%20Separation/Neuroscience_research_brochure.ashx on Dec. 10, 2013.*
Schmid and Anton 2003 "Role of integrins in the development of the cerebral cortex" Cerebral cortex 13:219-224.*
SFN 40th annual meeting abstracts 2010 "Rapid isolation of neural cell populations: advanced technologies in neuroscience" accessed from https://www.miltenyibiotec.com/~/media/Files/Navigation/Research/Neuroscience/SfN_2010_Abstract_Booklet.ashx on Dec. 10, 2013.*
Homologene 2014 "Genes identified as putative homologs of one another during the construction of homologene" downloaded from www.ncbi.nlm.nih.gov/homologene.*
Milner et al. 1997 "expression of àvβ3 and àvβ8 integrins during oligodendrocyte precursor differentiation in the presence and absence of axons" Glia 21:350-360.*
Smith and Giorgio 2004 "Quantitation and kinetics of CD51 surface receptor expression: implications for targeted delivery" Ann Biomed Eng 32(5):635-44 (abstract only).*
Barres, B.A. et al.(Nov. 1988). "Immunological, Morphological, and Electrophysiological Variation Among Retinal Ganglion Cells Purified by Panning," *Neuron.* 1:791-803.
Guez-Barber, D. et al. (Jan. 15, 2012). "FACS Purification of Immunolabeled Cell Types From Adult Rat Brain," *J Neurosci Methods* 203(1):10-18.
Hirsch, E. et al. (1994). "$\alpha_v$ Integrin Subunit Is Predominately Located in Nervous Tissue and Skeletal Muscle During Mouse Development," *Dev Dyn* 201:108-120.
Kawaguchi, S-Y. et al. (2006, e-pub. Nov. 22, 2005). "Integrin α3β1 Suppresses Long-Term Potentiation at Inhibitory Synapses on the Cerebellar Purkinje Neuron," *Mol. Cell. Neurosci.* 31:416-426.
Nolte, C. et al. (2001). "GFAP Promoter-Controlled EGFP Expressing Transgenic Mice: A Tool to Visualize Astrocytes and Astrogliosis in Living Brain Tissue," *Glia* 33:72-86.
Takada, Y. et al. (Jun. 1, 2007). "Protein Family Review. The Integrins," *Genome Biology* 8:215.1-215.9.
Tamamaki, N. et al. (2003, e-pub. Oct. 13, 2003). "Green Fluorescent Protein Expression and Colocalization With Calretinin, Parvalbumin and Somatostatin in the GAD67-GFP Knock-In Mouse," *J Comp Neurol* 467:60-79.
Tomomura, M. et al. (2001). "Purificiaton of Purkinje Cells by Fluorescence-Activiated Cell Sorting From Transgenic Mice That Express Green Fluorescent Protein," *Eur J Neurosci* 14:57-63.

(Continued)

*Primary Examiner* — Gregory S Emch
*Assistant Examiner* — Adam M Weidner
(74) *Attorney, Agent, or Firm* — Morrison & Foerster LLP (57) ABSTRACT

The present invention provides the use of the cell surface antigen CD51 as a negative selection marker for neuronal cells and a method for enrichment, isolation and/or detection of neuronal cells comprising the steps a) contacting a sample containing neuronal cells with an antigen-binding fragment specific for the CD51 antigen coupled to a solid phase, thereby labeling the CD51 positive cells of said sample and b) isolating the non-labeled cells of said sample.

7 Claims, 9 Drawing Sheets

(56) References Cited

OTHER PUBLICATIONS

Treese, C. et al. (2008, e-pub. Feb. 28, 2008). "Characterization of Fibroblasts Responsible for Cartilage Destruction in Arthritis," *Cytometry Part A* 73A:351-360.

Zhao, C. et al. (2009, e-pub. Sep. 8, 2009). "Up-Regulation of Oligodendrocyte Precursor Cell αV Integrin and Its Extracellular Ligands During Central Nervous System Remyelination," *Journal of Neuroscience Research* 87:3447-3455.

Zuo, Y. et al. (Dec. 8, 2004). "Fluorescent Proteins Expressed in Mouse Transgenic Lines Mark Subsets of Glia, Neurons, Macrophages, and Dendritic Cells for Vital Examination," *J Neurosci* 24(49):10999-11009.

Christopherson, K.S. et al. (2005). "Thrombospondins are Astrocyte-Secreted Proteins that Promote CNS Synaptogenesis," *Cell* 120(3):421-433.

Fields, R.D. et al. (2002). "New Insights into Neuron-Glia Communication," *Science* 298(5593):556-562.

Jungblut, M. et al. (Jul. 2012). "A Novel Method for Rapid Isolation of "Untouched" Neurons by Immunomagnetic Depletion of Non-Neuronal Cells," MACS Miltenyi Biotech, Poster, presented at *FENS*, 8th Annual Meeting, Barcelona, Spain, Jul. 14-18, 2012, one page.

Jungblut, M. et al. (Oct. 2012). "A Novel Method for Rapid Isolation of "Untouched" Neurons by Immunomagnetic Depletion of Non-Neuronal Cells," MACS Miltenyi Biotech, *Poster presented at SFN Annual Meeting*, New Orleans, LA, Oct. 13-17, 2012, one page.

Pfrieger, F.W. (2009). "Roles of Glial Cells in Synapse Development," *Cell Mol. Life Sci.* 66(13):2037-2047.

\* cited by examiner

SEPARATION OF LIVING UNTOUCHED NEURONS

CROSS-REFERENCE TO RELATED APPLICATIONS

This claims priority to European Application No.: EP12157671.4, filed Mar. 1, 2012, the contents of which are incorporated herein by reference in its entirety.

FIELD OF THE INVENTION

The present invention relates generally to the field of separating cells, in particular to processes for separation of untouched neuronal cells.

BACKGROUND OF THE INVENTION

A cell suspension that is obtained after dissociation of neural tissue comprises a wide variety of different cell types. But, selective targeting and isolation of a special cell type is often the prerequisite for experimental in vitro studies on these cells. Relatively easy techniques like density gradient centrifugation or isolation of living cells by culture conditions lead to low purities and massive cell loss.

A widely used approach in the field of neurobiology is the use of transgenic mice expressing a fluorescent protein controlled by a cell-type specific promoter in combination with fluorescence-activated cell sorting that facilitates isolation of a special cell population (Nolte et al., 2001: Glia 33:72-86; Tomomura et al., 2001: Eur J Neurosci 14:57-63; Tamamaki et al., 2003: J Comp Neurol 467, 60-79; Zuo et al., 2004: J Neurosci 24:10999-11009).

But, besides the need of transgenic mice and expensive equipment this procedure is quite cumbersome and takes several hours. Fluorescence-activated cell sorting of neurons was also described for non-transgenic animals, after labeling the cells with the neuron specific marker NeuN (Guez-Barber et al., 2012: J Neurosci Methods 203, 10-18). Nevertheless, this approach does not allow for the separation of living neurons as it requires labeling of an intracellular marker.

Another technique leading to isolation of neural cells was described by Barres et al. (1988: Neuron 1:791-803). The method named immunopanning uses an antibody mediated cell adhesion. Originally described for the isolation of Retinal cells using Thy-1 as specific marker for retinal ganglion cells, the method was also applied for the isolation of neurons (Cahoy et al., 2008: J Neurosci 28:264-278) by subsequent depletion of oligodendrocytes, microglia and astrocytes. But, an one step isolation for neurons using this technique has not been described so far.

A straightforward method for the isolation of a desired cell type is the magnetic separation of cells, e.g. the magnetic activated cell sorting (MACS technology, Miltenyi Biotec GmbH, Germany; U.S. Pat. No. 5,411,863, U.S. Pat. No. 5,543,289, U.S. Pat. No. 6,020,210, U.S. Pat. No. 6,417,011). This technology requires a marker that allows direct separation of the cells of interest by an antibody coupled to a magnetic microbead. However, a general neuron specific cell surface marker is not known so far and the direct magnetic cell sorting of viable neurons is therefore not applicable. Nevertheless, a negative isolation strategy can be applied to isolate cell populations that cannot be addressed directly. In this approach, non-target cells are magnetically labeled and depleted, thereby isolating the unlabeled cells of interest.

The object of the present invention is to provide an improved method for separating living neuronal cells and removing non-neuronal cells from a cell suspension derived from nervous tissue.

All references, publications, and patent applications disclosed herein are hereby incorporated by reference in their entirety.

SUMMARY OF THE INVENTION

The inventors surprisingly identified CD51 (Integrin alpha V) as a marker that is expressed by the majority of non-neuronal cells which are present in a cell suspension obtained from nervous tissue, e.g. astrocytes, astrocyte precursors, microglia, oligodendrocytes, oligodendrocyte precursors, endothelial cells, fibroblasts, and lymphocytes. Moreover, the inventors also identified CD51 as a marker that is expressed by the majority of non-neuronal cells which are present in spontaneously differentiated pluripotent cells. Therefore, this marker can be used as a pan-non-neuronal cell surface marker for the depletion of non-neuronal cells.

CD51 represents the integrin alpha chain V (UniProtKB acc. no. P43406 (mouse), P06756 (human)). It associates non-covalently with the B subunits of the integrin family including B1(CD29), B3 (CD61), B5 and B6 to form functional signaling complexes. Integrin alpha V is expressed by a variety of tissues during development and in the adult. It plays a crucial role in vasculogenesis, angiogenesis, wound healing, tumorigenesis, neurogenesis, and inflammation (Takada et al., 2007: Genome Biology 8:215.1-215.9). CD51 was also described to be expressed by fibroblasts (Treese et al., 2008: Cytometry A 73A:351-360) and by cells of the skeletal muscle (Hirsch et al., 1994: Dev Dyn 201:108-120). In the brain it was found to be crucial for neuron-glial adhesive interactions during neuronal migration in the cerebral cortex (Anton et al., 1999: Neuron 22:277-289).

The present invention provides the use of the antigen CD51 as a negative selection marker for neuronal cells.

A method for enrichment, isolation and/or detection of living neuronal cells comprises the steps a) contacting a sample containing neuronal cells with an antigen-binding fragment such as an antibody or an antibody fragment specific for the CD51 antigen coupled to a solid phase thereby labeling CD51 positive cells of said sample, and b) isolating the non-labeled cells of said sample, i.e. the cells which are not bound by the antigen-binding fragment specific for the CD51 antigen. These are the untouched target cells, i.e. the enriched neuronal cells substantially free of non-neuronal cells.

The purity can be further increased if an astrocyte specific cell surface marker is used in addition to CD51 to deplete a subpopulation of CD51 negative remaining astrocytes.

DETAILED DESCRIPTION OF THE INVENTION

Unexpectedly, the inventors found that CD51 is expressed by the majority of non-neuronal cells, including e.g. astrocytes, astrocyte precursors, microglia, oligodendrocytes, oligodendrocyte precursors, endothelial cells, and lymphocytes, but not by neurons (see Example 2). Therefore, surprisingly, the cell surface marker CD51 is well-suited as a negative selection marker for neuronal cells.

In a main aspect the present invention provides the use of CD51 as a negative selection marker for neuronal cells.

In one aspect the present invention provides a method for enrichment, isolation and/or detection of neuronal cells comprising the steps a) contacting a sample containing neuronal cells with an antigen-binding fragment specific for the CD51 antigen coupled to a solid phase thereby labeling the CD51 positive cells of said sample, b) isolating the non-labeled cells of said sample.

The non-labeled or untouched cells are the cells which are not bound by the antigen-binding fragment specific for the antigen CD51.

The purity can be further increased if an astrocyte specific cell surface marker is used in addition to CD51 to deplete a subpopulation of remaining astrocytes. Therefore, in one embodiment of the invention a method for enrichment and isolation of neuronal cells is provided that comprises the steps a) contacting a sample containing neuronal cells with an antigen-binding fragment specific for the CD51 antigen coupled to a solid phase and with an antigen-binding fragment specific for an astrocyte specific cell surface marker, e.g. ACSA-2 (ACSA: astrocyte cell surface antigen) or GLAST (ACSA-1) coupled to a solid phase, thereby labeling the CD51 positive cells and the cells expressing an astrocyte specific cell surface marker of said sample b) isolating the non-immobilised cells of said sample.

Contacting of the sample containing the neuronal cells with an antigen-binding fragment specific for the CD51 antigen and with an antigen-binding fragment specific for an astrocyte specific cell surface marker such as ACSA-2 or GLAST (ACSA-1) can be performed simultaneously or subsequently.

In a further aspect the present invention provides a substantially pure neuronal cell composition obtainable by the methods disclosed herein. The invention allows isolation of all neurons that are present in the mixed neural cell suspensions. The cell composition shows only minimal contamination by non-neuronal cells and comprises a variety of different neuronal subtype, which cannot be obtained by other methods of the prior art.

In an additional aspect the present invention provides a kit for enrichment, isolation and/or detection of neuronal cells comprising a) an antigen-binding fragment specific for the CD51 antigen coupled to a solid phase; and optionally in addition b) an antigen-binding fragment specific for an astrocyte specific cell surface marker such as ACSA-2 or GLAST (ACSA-1) coupled to a solid phase.

The cells achieved by the method of the present invention can be cultured and/or analysed (characterised) after enrichment according to all methods known to the person skilled in the art.

DEFINITIONS

Unless defined otherwise, technical and scientific terms used herein have the same meaning as commonly understood by one of ordinary skill in the art to which this invention belongs.

The term "sample" as used herein refers to a sample containing neuronal and non-neuronal cells in any ratio. Preferentially, these cells are viable. But, these cells can also be fixed cells which may be used for subsequent nucleic acids or protein extraction. The samples may be from animals, especially mammals such as mouse, rats or humans. Tissue derived from the nervous system, e.g. whole brain tissue, special brain regions, spinal cord, peripheral nervous tissue, embryonic stem (ES) cell derived or induced pluripotent stem (iPS) cell derived neural cells, or any tissue that contains neuronal cells can be used. The invention is illustrated mainly isolating neuronal cells from dissociated mouse brain tissue. However, it encompasses isolation of neuronal cells from any mammalian tissue in general using antibodies that detect the CD51 antigen.

Exemplary it is described in Example 9 that the expression profile of CD51 is equivalent in humans. All procedures of the embodiments of the present invention and the compositions obtainable by the methods can also be from human origin or any other species than mouse.

The term "target cells" as used herein refers to the cells which are the desired cells separated by the present invention. Regularly, the target cells are the non-labeled, CD51 negative neuronal cells generated by the process of the present invention.

The term "non-target cells" as used herein refers to the non-neuronal cells which are specifically bound by one antigen-binding fragment which is coupled to a solid phase.

The term "negative fraction" as used herein refers to the neuronal cells which are and are not bound by one antigen-binding fragment coupled to a solid phase and are the desired target cells.

The term "positive fraction" as used herein refers to the non-neuronal cells which are bound by one antigen-binding fragment coupled to a solid phase and are the undesired non-target cells.

The term "original fraction" as used herein refers to the mixed neural cell suspension before the cell separation containing the desired neuronal as well as non-neuronal cells.

The term "depletion" as used herein refers to a process of a negative selection that separates the desired neuronal cells from the undesired non-neuronal cells which are labeled by one antigen-binding fragment coupled to a solid phase.

The term "non-labeled" or "untouched" as used herein refers to the neuronal cells which are not bound by one antigen-binding fragment coupled to a solid phase. The non-labeled, untouched cell fraction contains the desired target cells.

The term "purity" as used herein refers to the percentage of CD51 or CD51/ACSA-2 negative cells in the negative cell fraction.

The term "neural" as used herein refers to all different subpopulations of cells derived from tissue of the nervous system containing neuronal and non-neuronal cells.

The term "marker" as used herein refers to a cell antigen that is specifically expressed by a certain cell type. Preferentially, the marker is a cell surface marker, so that enrichment, isolation and/or detection of living cells can be performed.

The term "solid phase" as used herein refers to the coupling of the antigen-binding fragment, e.g. an antibody, to other molecules, e.g. particles, fluorophores, haptens like biotin, or larger surfaces such as culture dishes and microtiterplates. In some cases the coupling results in direct immobilization of the antigen-binding fragment, e.g. if the antigen-binding fragment is coupled to a larger surface of a culture dish. In other cases this coupling results in indirect immobilisation, e.g. an antigen-binding fragment coupled directly or indirectly (via e.g. biotin) to a magnetic bead is immobilised if said bead is retained in a magnetic field. In further cases the coupling of the antigen-binding fragment to other molecules results not in a direct or indirect immobilization but allows for enrichment, separation, isolation, and detection of cells according to the present invention, e.g. if the antigen-binding fragment is coupled to a fluorophore which then allows discrimination of labeled cells and non-labeled cells, e.g. via flow cytometry methods, like FACSsorting, or fluorescence microscopy.

The term "particle" as used herein refers to a solid phase such as colloidal particles, microspheres, nanoparticles, or beads. Methods for generation of such particles are well known in the field of the art. The particles may be magnetic particles. The particles may be in a solution or suspension or they may be in a lyophilised state prior to use in the present invention. The lyophilized particle is then reconstituted in convenient buffer before contacting the sample to be processed regarding the present invention.

The term "magnetic" in "magnetic particle" as used herein refers to all subtypes of magnetic particles which can be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

The term "antigen-binding fragment" as used herein refers to any moiety that binds preferentially to the desired target molecule of the cell, i.e. the antigen. The term moiety comprises, e.g., an antibody or antibody fragment. The term "antibody" as used herein refers to polyclonal or monoclonal antibodies which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labeled antibodies). The term "antibody" comprises both intact molecules and antibody fragments, such as Fab, Fab', F(ab')2, Fv and single-chain antibodies. Additionally, the term "antigen-binding fragment" includes any moiety other than antibodies or antibody fragments that binds preferentially to the desired target molecule of the cell. Suitable moieties include, without limitation, oligonucleotides known as aptamers that bind to desired target molecules (Hermann and Pantel, 2000: Science 289: 820-825), carbohydrates, lectins or any other antigen binding protein (e.g. receptor-ligand interaction).

The linkage between antibody and particle can be covalent or non-covalent. A covalent linkage can be, e.g. the linkage to carboxyl-groups on polystyrene beads, or to $NH_2$ or $SH_2$ groups on modified beads. A non-covalent linkage is e.g. via biotin-avidin or a fluorophore-coupled-particle linked to anti-fluorophore antibody. Methods for coupling antibodies to particles, fluorophores, haptens like biotin or larger surfaces such as culture dishes are well known to the skilled person in the art.

As used herein and in the appended claims, the singular forms "a," "an," and "the" include plural reference unless the context clearly indicates otherwise. For example, reference to a "cell" is a reference to from one to many cells, such as a population of cells, and includes equivalents thereof known to those skilled in the art, and so forth.

As is understood by one skilled in the art, reference to "about" a value or parameter herein includes (and describes) embodiments that are directed to that value or parameter per se. For example, description referring to "about X" includes description of "X".

It is understood that aspect and variations of the invention described herein include "consisting" and/or "consisting essentially of" aspects and variations.

For enrichment, isolation or selection in principle any sorting technology can be used. This includes for example affinity chromatography or any other antibody-dependent separation technique known in the art. Any ligand-dependent separation technique known in the art may be used in conjunction with both positive and negative separation techniques that rely on the physical properties of the cells. An especially potent sorting technology is magnetic cell sorting. Methods to separate cells magnetically are commercially available e.g. from Invitrogen, Stem cell Technologies, in Cellpro, Seattle or Advanced Magnetics, Boston. For example, monoclonal antibodies can be directly coupled to magnetic polystyrene particles like Dynal M 450 or similar magnetic particles and used e.g. for cell separation. The Dynabeads technology is not column based, instead these magnetic beads with attached cells enjoy liquid phase kinetics in a sample tube, and the cells are isolated by placing the tube on a magnetic rack. However, in a preferred embodiment for enriching, sorting and/or detecting neuronal cells from a sample containing neuronal cells according the present invention monoclonal antibodies are used in conjunction with colloidal superparamagnetic microparticles having an organic coating by e.g. polysaccharides (Magnetic-activated cell sorting (MACS) technology (Miltenyi Biotec, Bergisch Gladbach, Germany)). These particles (nanobeads or MicroBeads) can be either directly conjugated to monoclonal antibodies or used in combination with anti-immunoglobulin, avidin or anti-hapten-specific MicroBeads.

The MACS technology allows cells to be separated by incubating them with magnetic nanoparticles coated with antibodies directed against a particular surface antigen. This causes the cells expressing this antigen to attach to the magnetic nanoparticles. Afterwards the cell solution is transferred on a column placed in a strong magnetic field. In this step, the cells attach to the nanoparticles (expressing the antigen) and stay on the column, while other cells (not expressing the antigen) flow through. With this method, the cells can be separated positively or negatively with respect to the particular antigen(s).

In case of a positive selection the cells expressing the antigen(s) of interest, which attached to the magnetic column, are washed out to a separate vessel, after removing the column from the magnetic field.

In case of a negative selection the antibody used is directed against surface antigen(s) which are known to be present on cells that are not of interest. After application of the cells/magnetic nanoparticles solution onto the column the cells expressing these antigens bind to the column and the fraction that goes through is collected, as it contains the cells of interest. As these cells are non-labeled by an antibody coupled to nanoparticels, they are "untouched".

The procedure can be performed using direct magnetic labeling or indirect magnetic labeling. For direct labeling the specific antibody is directly coupled to the magnetic particle. Indirect labeling is a convenient alternative when direct magnetic labeling is not possible or not desired. A primary antibody, a specific monoclonal or polyclonal antibody, a combination of primary antibodies, directed against any cell surface marker can be used for this labeling strategy. The primary antibody can either be unconjugated, biotinylated, or fluorophore-conjugated. The magnetic labeling is then achieved with anti-immunoglobulin MicroBeads, anti-biotin MicroBeads, or anti-fluorophore MicroBeads. The method of the present invention allows for both the direct magnetic labeling and the indirect magnetic labeling (see Example 3).

The term "substantially pure neuronal cell composition" as used herein refers to a cell composition containing at least 80%, more preferentially at least 90%, most preferentially at least 95% of CD51 or CD51/ACSA (astrocyte cell surface antigen) negative cells in the target cell fraction. CD51 negative cells are in the target cell fraction if the method of the present invention is performed by using an antigen-binding fragment specific for the CD51 antigen. CD51/ACSA negative cells are in the target cell fraction if the method of the present invention is performed by using an antigen-binding fragment specific for the CD51 antigen and an antigen-binding fragment specific for an astrocyte specific surface marker, e.g. ACSA-2 or GLAST (ACSA-1).

Normally, neuronal cells are integrated in a network of different cell types in vivo. To make them accessible to enrichment and sorting techniques the tissue has to be dissociated before use of such methods.

In the present invention, brain tissue is enzymatically dissociated with a trypsin or papain based procedure using e.g. the MACS® Neural Tissue Dissociation Kit (T) (NTDK (T)) or the MACS® Neural Tissue Dissociation Kit (P) (NTDK (P)) (Miltenyi Biotec). The tissue is further mechanically dissociated manually or with an instrument that allows automated tissue dissociation, e.g. gentleMACS™ Dissociator (Miltenyi Biotec). Other methods that allow generation of a viable single cell suspension from neural tissue can also be used and are well known by the person skilled in the art.

The neuronal cells obtainable by the methods disclosed herein may be used for subsequent steps such as research, diagnostics, pharmacological or clinical applications known to the person skilled in the art. Purification of neurons from the variety of other cell types in the brain, is a prerequisite for molecular, biochemical or electrophysiological in vitro analysis. Cells can be taken into culture using a Medium optimized for this application, e.g. MACS® Neuro Medium supplemented with MACS® Supplement B27 PLUS (Miltenyi Biotec). In the present invention isolated cells were seeded onto poly-L-lysine-coated glass coverslips and maintained in a humidified atmosphere (5% $CO_2$, 95% air) at 37° C. for 1 week using MACS® Neuro Medium (Miltenyi Biotec) supplemented with MACS® Supplement B27 PLUS (Miltenyi Biotec) and L-glutamine (0.5 mM, Invitrogen).

Such neuronal cell cultures can be used to study e.g. neural development, synaptogenesis, cell signaling, neurotransmitter release, or to perform electrophysiological measurements for the investigation of neural activity.

The enriched neuronal cells can be also used before and/or after cell culturing as a pharmaceutical composition in the therapy, e.g. cellular therapy, or prevention of diseases. The pharmaceutical composition can be used for the treatment and/or prevention of diseases in mammals, especially humans, possibly including administration of a pharmaceutically effective amount of the pharmaceutical composition to the mammal.

The disease may be any disease, which can be treated and/or prevented through the presence of neuronal cells and/or through increasing the concentration of the relevant cells in/at the relevant place, i.e. the brain or spinal cord. The treated and/or preventively treated disease may be any brain disorder, e.g. a degenerative disorder of neurons of a particular area of the central nervous system. The treatment may be the transplantation of enriched neuronal cells to the relevant place of the brain.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

Embodiments

Methods which allow for the use of a negative selection marker for enrichment, isolation and/or detection of cells are e.g. magnetic cell separation methods, immunopanning, and FACS sorting.

The antigen binding fragments may be labeled with particles, e.g. magnetic particles, haptens like biotin, or fluorophores. The antigen binding fragments may be immobilised, e.g. by attaching them on the surface of culture dishes or by labeling them with particles such as magnetic beads.

In one embodiment of the present invention the antigen-binding fragment is a CD51 antibody labeled with magnetic particles (CD51 MicroBeads). The coupling of antibody and particle may be covalent or non-covalent. If the coupling is covalent, the CD51 antibody is directly coupled to the magnetic particle. If the coupling is non-covalent, the particle is e.g. an anti-Biotin MicroBead or a Streptavidin MicroBead and the CD51 antibody is biotinylated. The sample, e.g. the labeled neural cell is loaded onto a column which is placed in a magnetic field. The magnetically labeled non-neuronal cells retain within the column and the flow through contains the untouched enriched neurons. Cultivation of these cells leads to a neuronal cell fraction with only a low percentage of contaminating non-neuronal cells (<10%) (see Example 5).

In another embodiment of the present invention the antigen binding fragments are an anti-CD51 antibody and an antibody specific for an astrocyte specific cell surface marker such as ACSA-2 or GLAST (ACSA-1). These antibodies are coupled covalently to magnetic particles. The sample, e.g. the neural cell suspension is labeled simultaneously with the Anti-CD51 MicroBeads and e.g. the Anti-ACSA-2 MicroBeads and loaded onto a column which is placed in a magnetic field. The magnetically labeled non-neuronal cells retain within the column and the flow through contains the untouched enriched neurons. Cultivation of these cells leads to a neuronal cell fraction that shows only a low percentage of contaminating non-neuronal cells (<5%). In a variant of this embodiment the anti-CD51 antibody and the antibody specific for an astrocyte specific cell surface marker are coupled to the same magnetic particle.

In another embodiment of the present invention the antigen binding fragments are an anti-CD51 antibody and an antibody specific for an astrocyte specific cell surface marker such as ACSA-2 or GLAST (ACSA-1). These antibodies are coupled covalently to magnetic particles. The sample, e.g. the neural cell suspension is labeled first with the CD51 Micro- Beads and loaded onto a column which is placed in a magnetic field. The magnetically labeled non-neuronal cells retain within the column and the flow through contains the untouched enriched neurons. Then, the flow through is labeled with the astrocyte specific MicroBeads and loaded onto a second column which is placed in a magnetic field. The magnetically labeled astrocytes retain within the column and the flow through contains the further enriched neurons. In a variant of this embodiment the order of labeling the sample containing neuronal cells is altered to the first labeling with e.g. the Anti-ACSA-2 Microbeads and thereafter with the CD51 MicroBeads.

In another embodiment of the present invention the antigen binding fragments are an anti-CD51 antibody and an antibody specific for an astrocyte specific cell surface marker such ACSA-2 or GLAST (ACSA-1). These antibodies are biotinylated. The sample, e.g. the neural cell suspension is labeled simultaneously or subsequently with the CD51-Biotin and e.g. the Anti-ACSA-2-Biotin. The magnetic labeling is then achieved with anti-Biotin MicroBeads or Streptavidin MicroBeads and the cells are loaded onto a column which is placed in a magnetic field. The magnetically labeled non-neuronal cells retain within the column and the flow through contains the untouched enriched neurons. Cultivation of these cells leads to a neuronal cell fraction that shows only a low percentage of contaminating non-neuronal cells (<5%) (see Example 8).

In another embodiment of the present invention the sample containing neural cells is depleted of CD51 negative cells using immunopanning with CD51 antibodies. The CD51 antibody is immobilised on the surface of a panning plate, e.g. a petri dish or a multi-well dish. The sample containing the neuronal cells in panning buffer is incubated on the CD51 panning plate to bind CD51 expressing cells. The non-adherent cells are harvested, e.g. by centrifugation and resuspended in e.g. cell culture medium for subsequent use.

To increase purity of neuronal cells the cells may further be depleted of astrocytes after depletion of CD51 positive cells using an astrocyte panning plate, i.e. a plate on which an antibody specific for an astrocyte marker such as ACSA-2 or GLAST (ACSA-1) is immobilised.

In another embodiment of the present invention the sample containing the neuronal cells is labeled with a fluorescently tagged CD51 antibody (and optionally with a further fluorescently tagged antibody specific for astrocyte specific markers) and subjected to a flow cytometry method, e.g. fluorescence-activated cell sorting (FACS).

The cell separation components necessary to perform the methods disclosed herein may be provided as a kit. Each kit contains the components necessary to perform the separation of desired cells from a sample containing neuronal cells. A kit for enrichment, isolation and/or detection of neuronal cells comprises a) an antigen-binding fragment specific for the CD51 antigen coupled to a solid phase; and optionally b) an antigen-binding fragment specific for an astrocyte specific cell surface marker coupled to a solid phase.

For use in magnetic cell sorting the antigen binding fragments are coupled to magnetic particles as described herein. The magnetic particles, e.g. MicroBeads, of the kit may be in a solution or suspension or they may be in a lyophilized state prior to use in a method of the present invention. The lyophilized particle is then reconstituted in convenient buffer before contacting with the sample containing neuronal cells to be processed regarding the present invention.

The antigen-binding fragment specific for an astrocyte specific cell surface marker may be Anti-ACSA-2 or Anti-GLAST (ACSA-1). Preferentially the astrocyte specific cell surface marker is ACSA-2.

EXAMPLES

Hereinafter, the present invention is described in more detail and specifically with reference to the examples, which however are not intended to limit the present invention.

Example 1

CD51 Expression in Postnatal Mouse Brain Tissue

Mouse brain tissue derived from P6 CD1 mice was dissociated with a trypsin or papain based procedure using the MACS® Neural Tissue Dissociation Kit (T) (NTDK (T)) or the MACS® Neural Tissue Dissociation Kit (P) (NTDK (P)) (Miltenyi Biotec) in combination with the gentleMACS™ Dissociator (Miltenyi Biotec) according to the manufacturer's instructions. Single cell suspensions were stained with the CD51 antibody conjugated to APC or PE for flow cytometric analysis. To avoid false-positive staining due to Fc receptor interactions, the FcR Blocking Reagent, mouse (Miltenyi Biotec) was applied prior to antibody labeling. Cell debris and dead cells (identified by propidium iodide) were excluded from the analysis. Data was acquired on a MACSQuant® Analyzer (Miltenyi Biotec).

Figure 1:
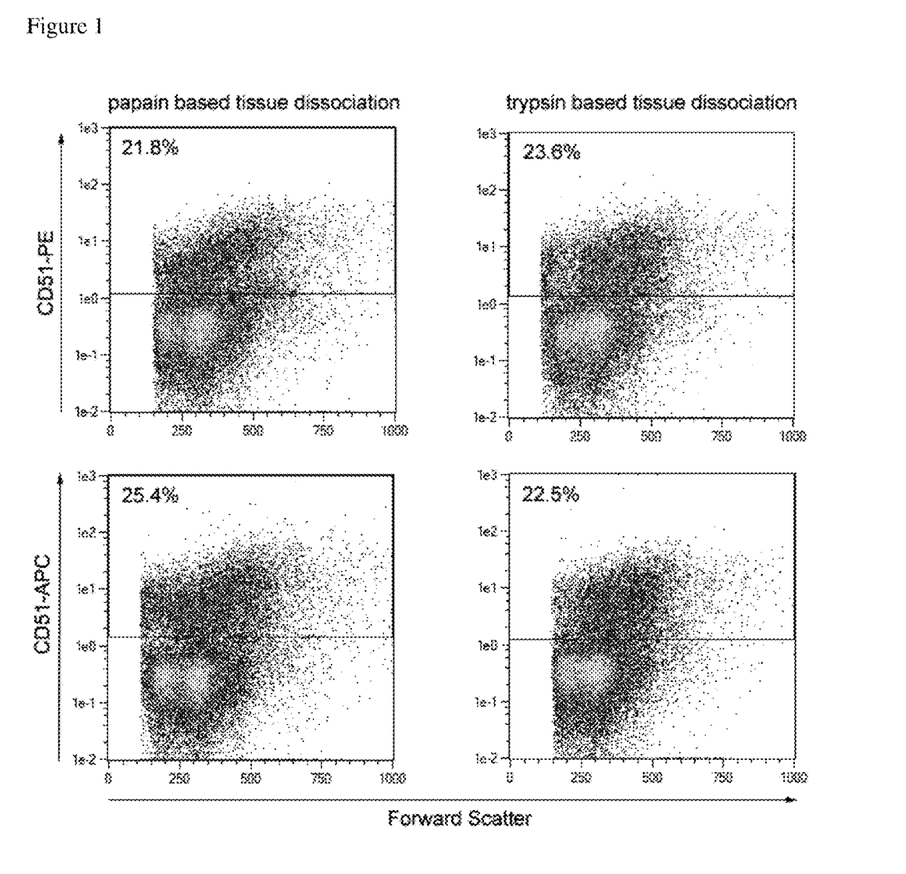
FIG. 1 shows flow cytometric analysis of CD51 expression in dissociated postnatal mouse brain tissue.

CD51 positive cells were detected in trypsin as well as papain dissociated brain tissue with a percentage of 21.8-25.4%. The percentage of CD51 positive cells slightly differed depending on the antibody conjugate and the enzyme used for dissociation, but no significant differences were detected. This experiment shows that the CD51 antigen shows neither papain nor trypsin sensitivity and CD51 positive cells can be clearly discriminated from CD51 negative cells in a cell suspension obtained from mouse brain tissue (see FIG. 1).

Example 2

Flow Cytometric Characterization of CD51 Positive Cells in Postnatal Mouse Brain Tissue Mouse brain tissue derived from P1, P2, or P3 CD1 mice was dissociated as described before using the NTDK(T) or (P). The resulting single cell suspension was co-stained with CD51 and markers specific for different neural subpopulations and subjected to flow cytometric analysis. For staining of the protease-sensitive epitopes CD31 and AN2, the cell suspension was incubated for 2 h at 37° C. in MACS® Neuro Medium +MACS® Supplement B27 PLUS under continuous rotation to re-express the epitopes. Due to the lack of markers that allow marking of living neuronal cell populations, GAD67-GFP transgenic mice were used to detect GABAergic neurons by their expression of GFP (green fluorescent protein). The analysis showed that GAD67-GFP positive GABAergic neurons lacked CD51 expression. Furthermore, neuronal progenitor cells, identified by PSA-NCAM expression, were identified as CD51 negative (see FIG. 2A).

Figure 2A:
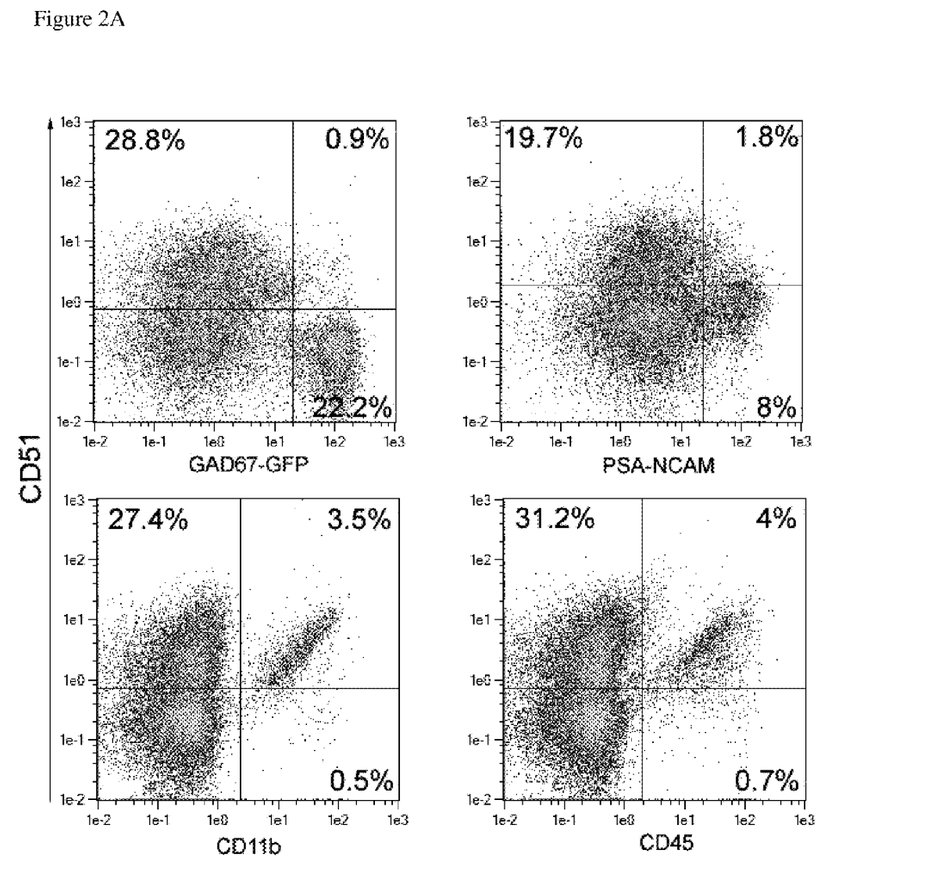
FIGS. 2A and 2B show flow cytometric characterization of CD51 expression in different neural cell types in dissociated postnatal mouse brain by co-staining of CD51 and markers specific for different neural subpopulations.
Figure 2B:
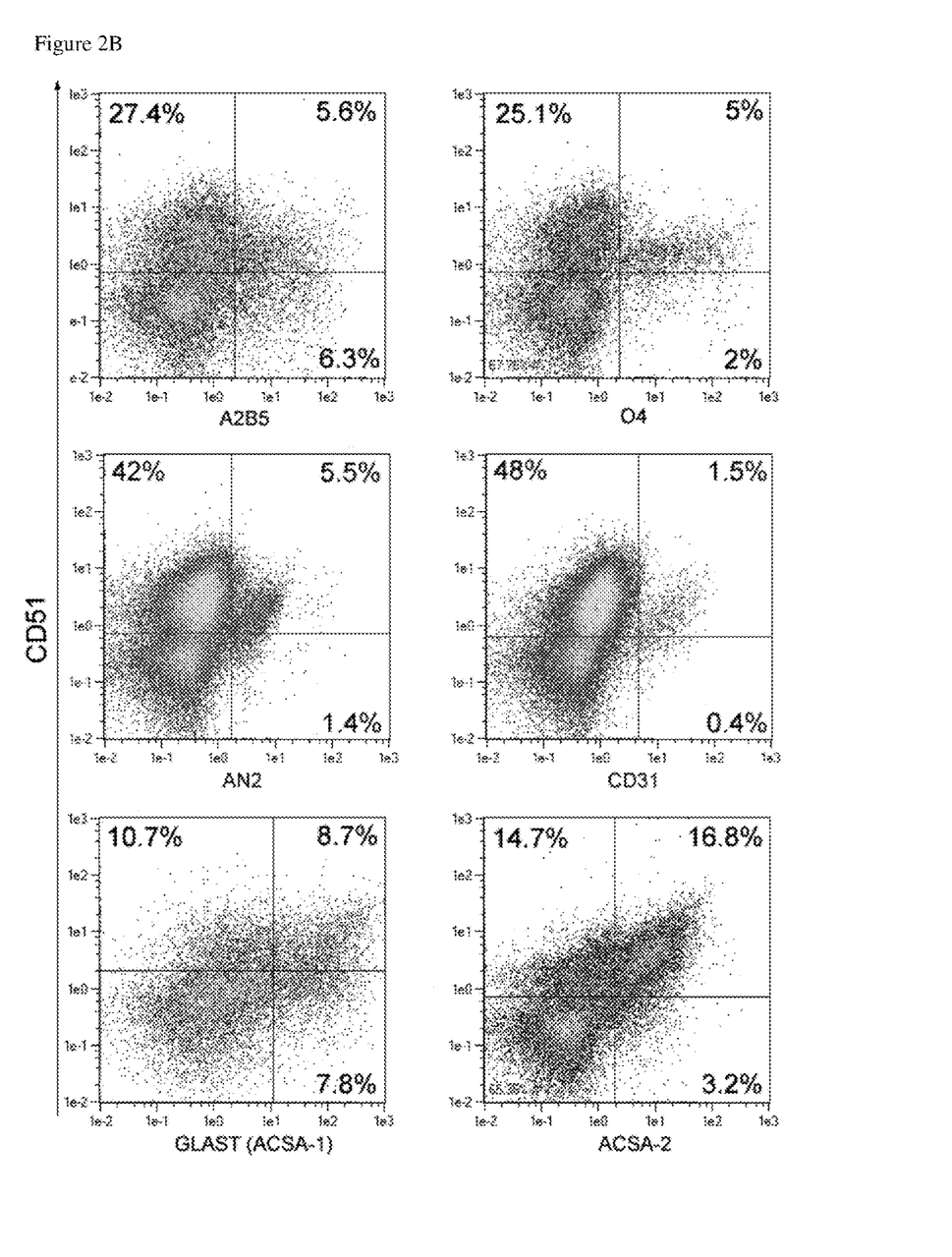

In comparison, CD11b-positive microglia, CD45 positive lymphocytes, AN2-positive oligodendrocyte precursors, O4-positive oligodendrocytes, as well as CD31 positive endothelial cells were detected by CD51 (see FIGS. 2A and B). In case of AN2 and CD31 staining, the total percentage of CD51 positive cells increased due to the treatment for reexpression of the AN2 and CD31 epitopes. The majority of astrocytes, which were identified by astrocyte specific antibodies Anti-GLAST (ACSA-1) and Anti-ACSA-2, were also CD51 positive. Approximately 50% of A2B5 positive progenitor cells showed CD51 expression (see FIG. 2B). All antibody conjugates used in this analysis are available at Miltenyi Biotec GmbH, Bergisch Gladbach, Germany.

Example 3

Depletion of CD51 Positive Cells By Magnetic Cell Separation

For depletion of CD51 positive non-neuronal cells a direct labeling strategy was compared to an indirect labeling with respect to purity and recovery of the target cells. For the direct labeling a CD51 specific antibody was covalently conjugated to magnetic particles.

The generation of superparamagnetic particles as used herein is disclosed in U.S. Pat. No. 5,543,289 which is included herewith by reference. Monoclonal antibodies recognizing the CD51 antigen were covalently conjugated to magnetic beads, resulting in 25 µg antibody per mL of bead suspension at a concentration of OD450=10.

Different concentrations of bead conjugated antibodies (0.75, 1.5, 3, 6 OD450/ml) were given to 100 µl of a neural cell suspension containing $1 \times 10^7$ cells. Cells were incubated for 15 minutes at 4° C., washed once with 1 ml PBS+0.5% BSA buffer, then resuspended in 1 ml of the same buffer and loaded on an LD column placed in the magnetic field of a MidiMACS™ Separator (Miltenyi Biotec). The column was washed twice with 1 ml of the same buffer. The magnetically labeled CD51 positive cells were retained within the column, whereas the flow through contained the CD51 negative target cells. CD51 positive cells retained within the column and were eluted as positively selected cell fraction after removing the column from the magnet.

Figure 3A:
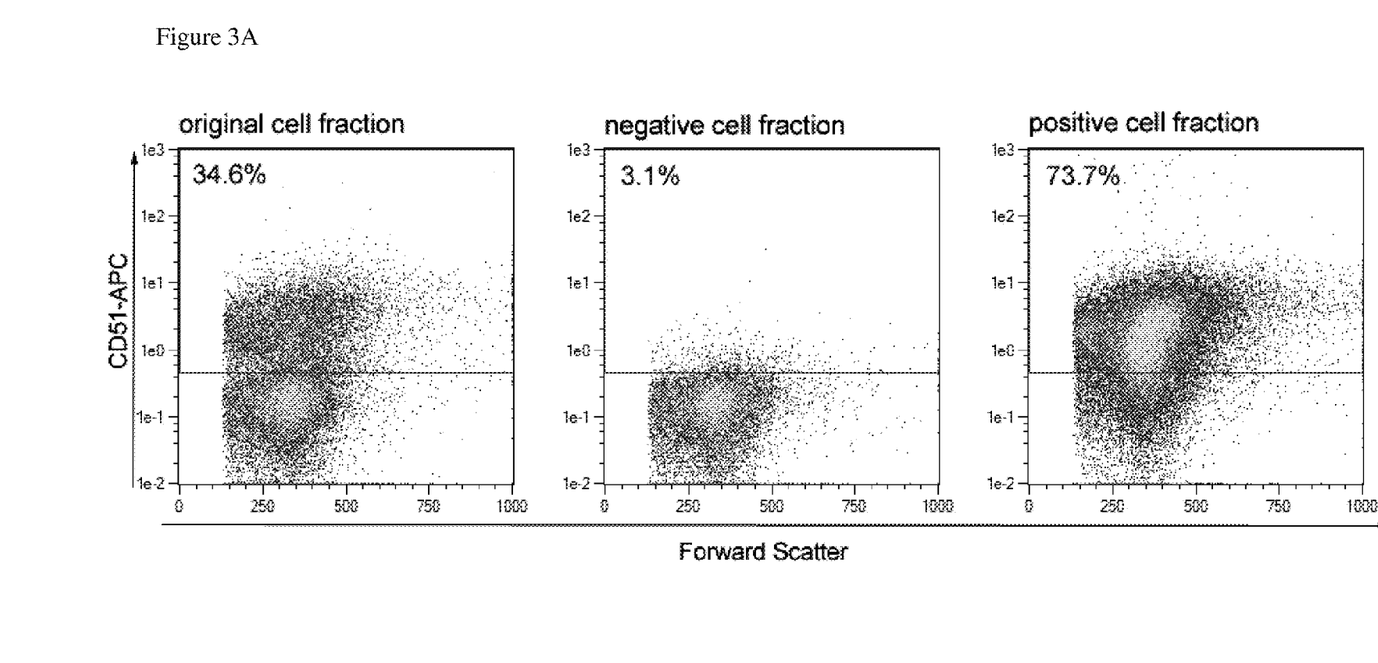
FIGS. 3A and 3B show depletion of CD51 positive cells by magnetic cell separation using a direct (A) or indirect (B) labeling strategy.

To determine the depletion efficiency the original as well as the negative and positive cell fraction were stained with CD51-APC and analyzed by flow cytometry. A MicroBead concentration of 3 OD450/ml resulted in a high purity of CD51 negative cells. FIG. 3A shows the original, negative, and positive fraction of one representative experiment. 96.7±0.5% of the cells in the negative cell fraction were identified as CD51 negative. 88.4±2.2% of the target cells contained in the original fraction were collected in the negative fraction. One representative experiment is shown in FIG. 3A.

Figure 3B:
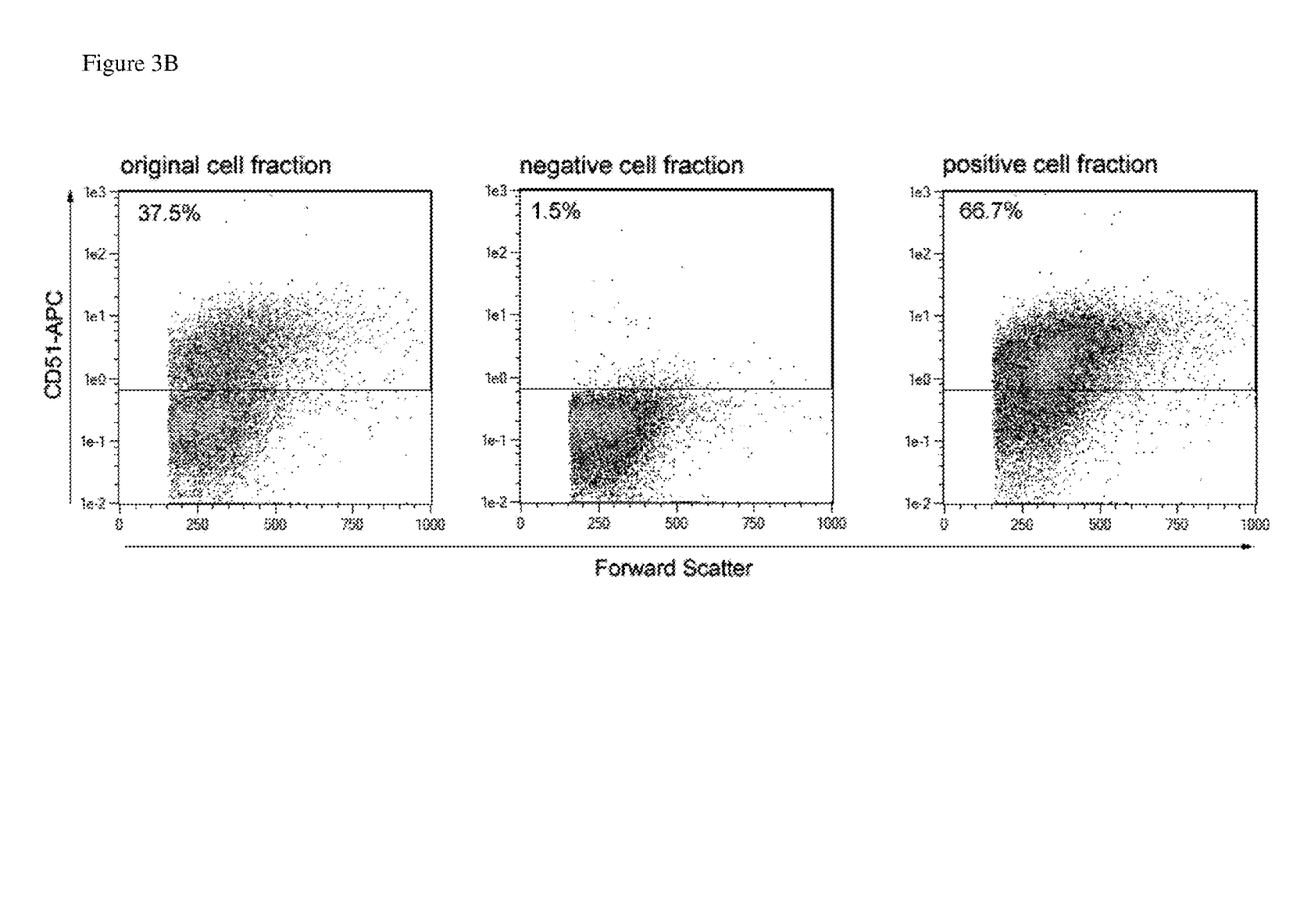

Furthermore, an indirect labeling strategy was tested. Therefore, $1 \times 10^7$ cells were first labeled with the biotinylated CD51 specific antibody for 10 minutes and washed once with 1 ml PBS+0.5% BSA buffer. Then, superparamagnetic MicroBeads coupled to an Anti-Biotin antibody were applied. Cells were incubated for 15 minutes at 4° C. and then washed once. Separation was carried out as described before. Different concentrations of the CD51-Biotin conjugate were tested (1, 2, 4, 6, 8 µg/ml). The highest purity of CD51 negative cells was obtained with a CD51-Biotin concentration of 6 µg/ml. One representative experiment is shown in FIG. 3B.

Analysis showed that 98.6±0.17% of the cells in the negative cell fraction were CD51 negative. Recovery of the target cells was 76.7±2.6% (see FIG. 3B).

Example 4

Efficient Depletion of Non-Neuronal Cells

Figure 4A:
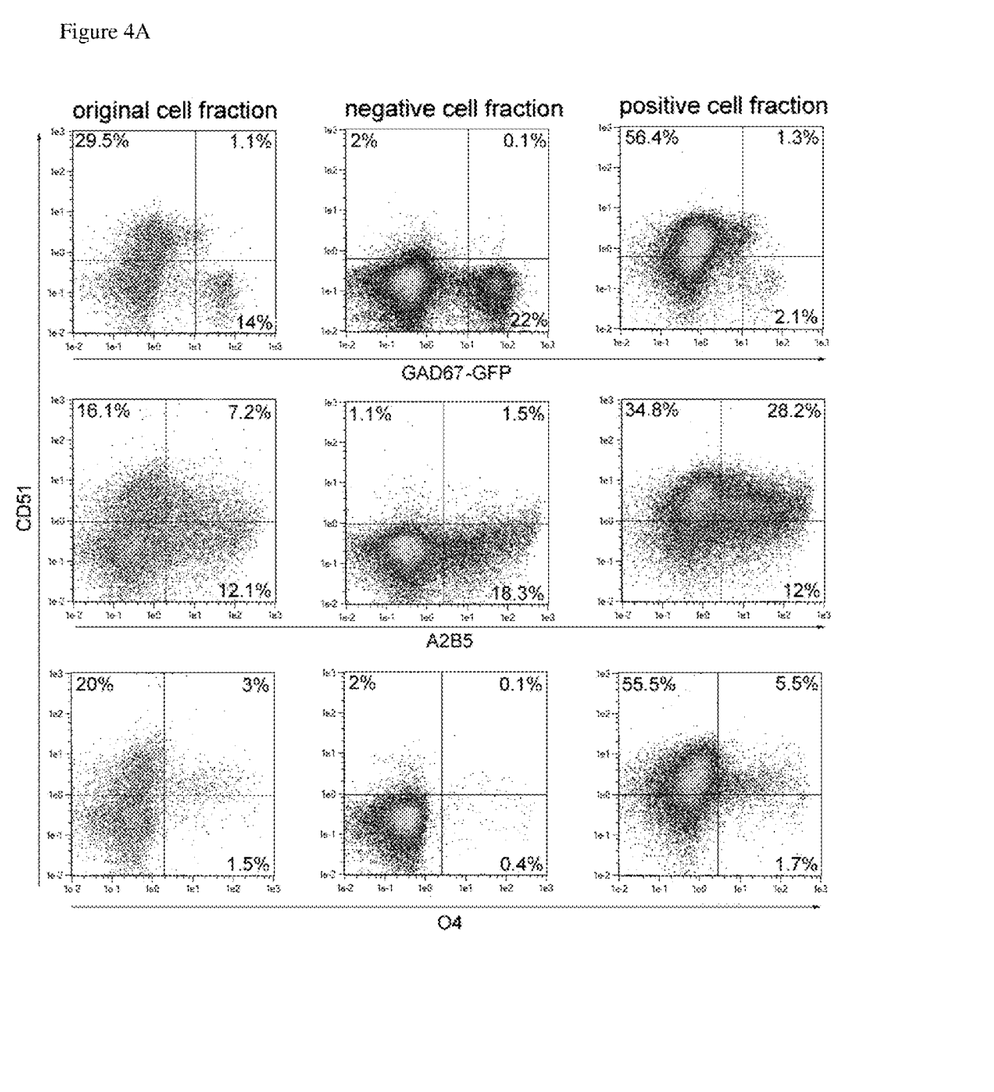
FIGS. 4A and 4B show efficient depletion of non-neuronal subpopulations by CD51-Biotin and Anti-Biotin Micro-Beads.
Figure 4B:
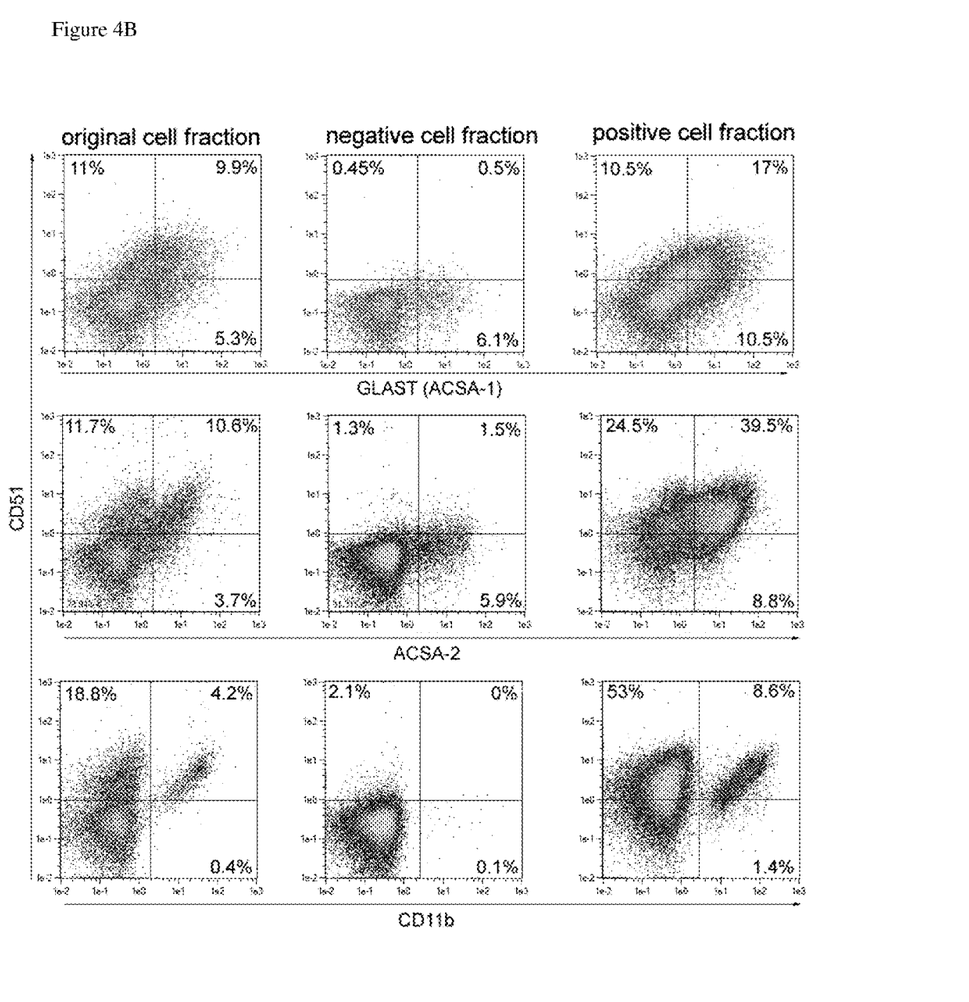

CD51 positive cells were depleted using whole mouse brain derived from P2 or P3 CD1 mice and an indirect labeling strategy as described before. The original, negative as well as positive cell fraction were co-stained with CD51 and exemplary A2B5, O4, GLAST (ACSA-1), ACSA-2, CD11b specific antibodies to determine the percentage of different neural subtypes in the original, negative as well as positive cell fraction. Use of GAD67-GFP mice allowed detection of GABAergic neurons. FIG. 4A shows that GAD67-GFP positive GABAergic neurons were enriched in the negative target cell fraction, whereas non-neuronal cells, like AN2 positive oligodendrocyte precursors, O4 positive oligodendrocytes, and CD11b positive microglia were depleted and found in the positive fraction (see FIGS. 4A,B). The majority of GLAST (ACSA-1) and ACSA-2 positive astrocytes was also depleted, but approximately 6% of these cells retain within the negative fraction (see FIG. 4B). All antibody conjugates used within this analysis are available at Miltenyi Biotec GmbH, Bergisch Gladbach, Germany.

Example 5

Cultivation of the Negative Cell Fraction

Cortical hemispheres were obtained from 1 day old mice and dissociated using the NTDK (P). CD51 positive cells were labeled using the biotinylated primary CD51 specific antibody at a concentration of 6 µg/ml and Anti-Biotin MicroBeads and then depleted as described before. The negative as well as the positive cell fraction was cultivated. Therefore, cells were seeded onto poly-L-lysine-coated glass coverslips and maintained in a humidified atmosphere (5% $CO_2$, 95% air) at 37° C. for 5 days using e.g. MACS® Neuro Medium (Miltenyi Biotec) supplemented with MACS® Supplement B27 PLUS (Miltenyi Biotec) and L-glutamine (0.5 mM, Invitrogen). Cultures were then fixed with 4% paraformaldehyde (PFA) in PBS (pH 7.4) for 20 min at 4° C. For immunostaining primary antibodies against GLAST (ACSA-1, mouse IgG2a, Miltenyi Biotec), GFAP (mouse IgG1, Millipore), Myelin Basic Protein (MBP) (mouse IgG2a, Millipore), and Microtubuli-Associated Protein 2 (MAP2) (rabbit polyclonal, Millipore) were applied overnight at 4° C. or for 3 h at room temperature. After rinsing 3 times with PBS, samples were incubated for 3 h at 4° C. or 1 h at room temperature with the corresponding secondary antibodies (Invitrogen). Cover slips were mounted onto glass slides using fluorescence mounting medium (Dako) and samples were analyzed by confocal fluorescence microscopy (Leica TCS SP2).

MAP2 immunostaining detected a lot of neurons in the negative cells fraction and only few neurons in the positive fraction. Co-staining for MAP2 and the astrocyte specific markers GFAP as well as GLAST (ACSA-1) showed that that some astrocytes were found in the negative fraction, but far more were detected in the positive fraction. Almost no MBP positive oligodendrocytes were detected in the negative fraction and mainly found in the positive fraction. The percentage of contaminating astrocytes and oligodendrocytes was <10%.

Example 6

Increase of the Purity Using an Astrocyte-Specific Marker in Addition to CD51

Whole mouse brain tissue derived from P3 CD1 mice was dissociated using the NTDK (P) as described before. To further increase the purity of the neuronal cell fraction and to deplete also the contaminating astrocytes, the astrocyte specific antibody Anti-ACSA-2 was used in combination with CD51 at different concentrations. Therefore, different concentrations of the biotin conjugated CD51 and Anti-ACSA-2 antibody were applied simultaneously to 100 µl of a neural cell suspension containing $1 \times 10^7$ cells and then incubated for 10 minutes at 4° C. Cells were then further processed and separated using one LD Column as described before.

Figure 5:
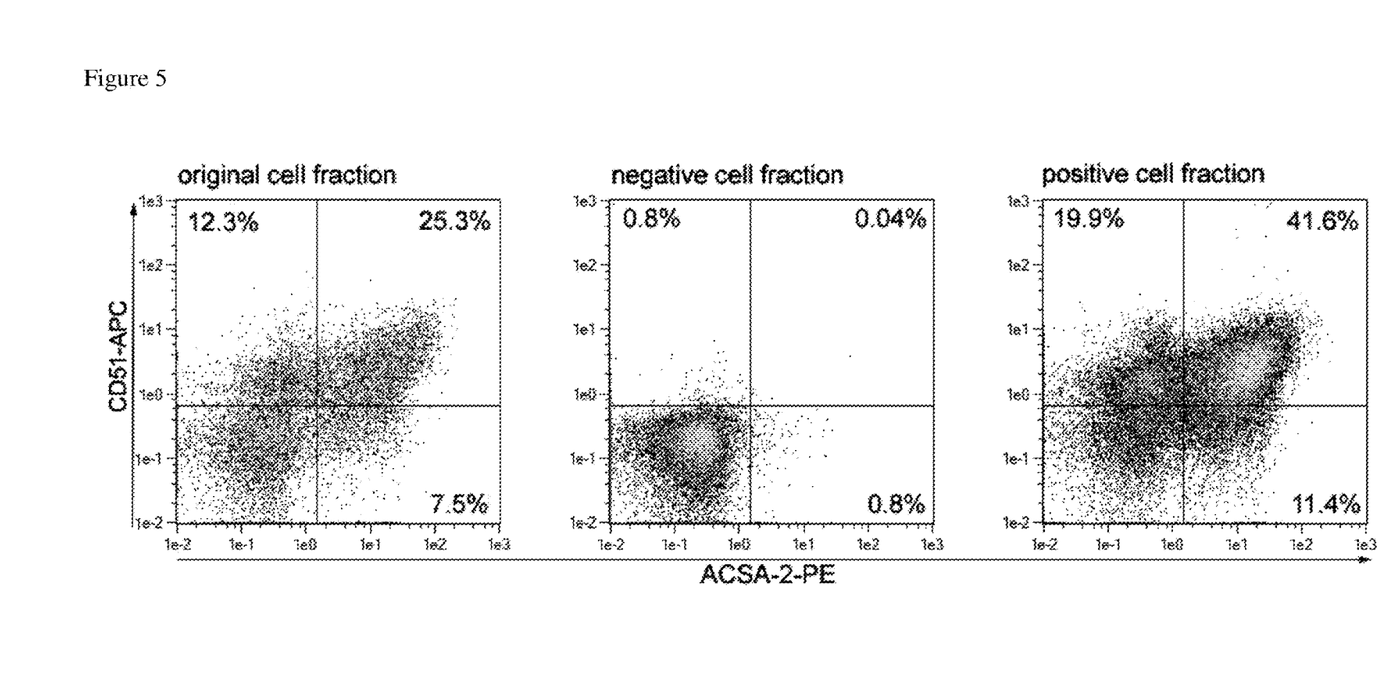
FIG. 5 shows an increase of the purity by using an astrocyte-specific marker in combination with CD51.

To determine depletion efficiency, the original as well as the negative and positive cell fraction were stained with the fluorochrome conjugated CD51 and Anti-ACSA-2 antibody and then analyzed by flow cytometry. The best purity and recovery of target cells was obtained when a concentration of 4 µg/ml of the CD51-Biotin conjugate and a concentration of 1 µg/ml of the Anti-ACSA-2-Biotin was applied. FIG. 5 shows one representative experiment. CD51/ACSA-2 positive cells detected in the original fraction were almost completely depleted in the negative target cell fraction (see FIG. 5). The average purity of CD51/ACSA-2 negative cells obtained with this antibody composition was 98.55±1.2%, whereas 69.5±3.15% of the target cells were recovered in the negative fraction.

Example 7

Separation of Neurons From Different Brain Regions

Figure 6:
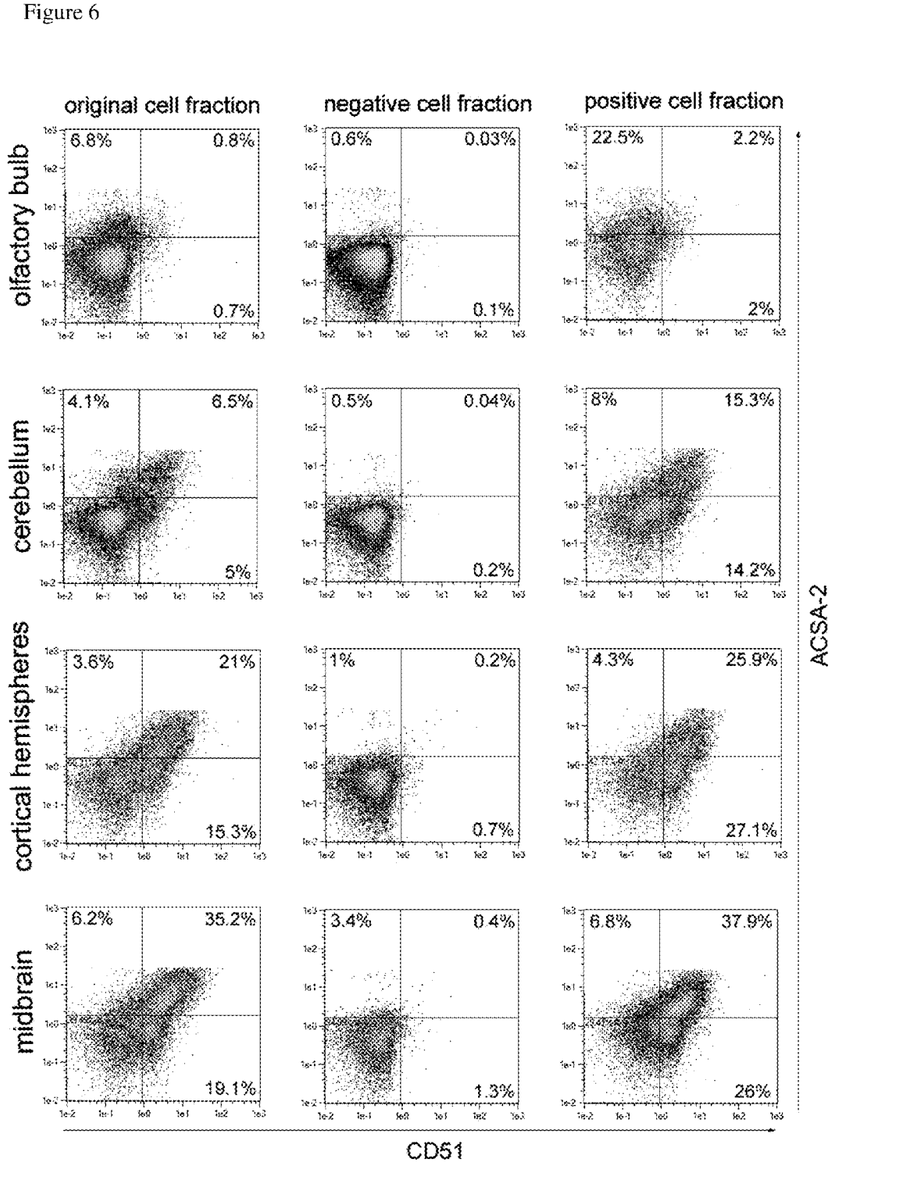
FIG. 6 shows isolation of neurons from different brain regions using CD51-Biotin and Anti-Biotin MicroBeads.

Brains from P4 CD1 mice were removed and cortical hermispheres, cerebellum, midbrain, or olfactory bulb were dissociated separately using the NTDK (P). Cells were labeled as described before with the CD51 and Anti-ACSA-2-Biotin conjugated antibodies at a concentration of 4 µg/ml and 1 µg/ml, respectively. Then, Anti-Biotin MicroBeads were applied for 15 minutes. After the separation, the original, negative as well as positive cell fraction were stained with ACSA-2 and CD51 specific fluorochrome conjugated antibodies and analysed by flow cytometry to determine purity. The frequency of CD51 and ACSA-2 positive cells differed in the original cell fraction depending on the brain region. In case of neural cells derived from olfactory bulb tissue, CD51/ACSA-2 positive cells showed a percentage of only 8%. In the cerebellum the percentage increased to approximately 15%, whereas in case of cortical hemispheres 40% and in midbrain even 60% of all cells were CD51/ACSA-2 positive non-neuronal cells. Nevertheless, purity of neuronal cells in the negative fraction was around 99% in case of olfactory bulb, cerebellum and cortical hemispheres and 97% for midbrain tissue (see FIG. 6).

Example 8

Cultivation of Neuronal Cells Isolated from Mouse Brain Tissue Derived from Mice of Different Age Cortical hemispheres were obtained from 1, 3 or 5 day old mice and dissociated using the NTDK (P). Cells were indirectly labeled and separated as described before with the CD51 and Anti-ACSA-2 biotinylated antibodies first and then Anti-Biotin MicroBeads. The negative as well as the positive cell fraction was cultivated. Therefore, cells were seeded onto poly-L-lysine-coated glass coverslips and maintained in a humidified atmosphere (5% $CO_2$, 95% air) at 37° C. for 5 days using e.g. MACS® Neuro Medium (Miltenyi Biotec) supplemented with MACS® Supplement B27 PLUS (Miltenyi Biotec) and L-glutamine (0.5 mM, Invitrogen). Cultures were then fixed with 4% paraformaldehyde (PFA) in PBS (pH 7.4) for 20 min at 4° C. For immunostaining, primary antibodies against GLAST (ACSA-1, mouse IgG2a, Miltenyi Biotec), GFAP (mouse IgG1, Millipore), Myelin Basic Protein (MBP) (mouse IgG2a, Millipore), Microtubuli-Associated Protein 2 (MAP2) (rabbit polyclonal, Millipore), and NeuN (mouse IgG1, Millipore) were applied overnight at 4° C. or for 3 h at room temperature. After rinsing 3 times with PBS, samples were incubated for 3 h at 4° C. or 1 h at room temperature with the corresponding secondary antibodies (Invitrogen). Cover slips were mounted onto glass slides using fluorescence mounting medium (Dako) and samples were analyzed by confocal fluorescence microscopy (Leica TCS SP2).

Immunostaining of the negative as well as positive cell fraction showed that mainly neurons identified by MAP2 and NeuN immunostaining were present in the neuronal cell fraction. Only a very low number of contaminating GLAST or GFAP positive astrocytes and MBP positive oligodendrocytes was detected in the target cell fraction (<5%). Neurons isolated from P1, P3, and P7 mouse brain tissue were successfully cultivated (see FIG. 8).

Example 9

CD51 Expression in Human Induced Pluripotent Stem (iPS) Cell Derived Neural Cells Immunocytochemical staining experiments using human induced pluripotent stem (iPS) cells that were maintained under conditions promoting spontaneous differentiation showed that neurons identified by MAP2 and NeuN immunostaining lacked CD51 immunoreactivity. In contrast, non-neuronal cells like astrocytes and oligodendrocytes were found to express CD51.

What is claimed is:
1. A method for enrichment, isolation and/or detection of mouse or human neuronal cells comprising the steps:
   a) contacting a sample containing neuronal cells with an antigen-binding fragment specific for the CD51 antigen coupled to a solid phase, thereby labeling the CD51 positive cells of said sample
   b) isolating the non-labeled cells of said sample.
2. The method of claim 1 wherein said sample in step a) is contacted simultaneously with an antigen-binding fragment specific for the CD51 antigen coupled to a solid phase and with an antigen-binding fragment specific for an astrocyte specific cell surface marker coupled to a solid surface, thereby labeling the CD51 positive cells and the cells expressing an astrocyte specific surface marker of said sample.
3. The method of claim 1, wherein the method comprises the additional steps subsequent to step a) and b):
   c) contacting the non-labeled cells of step b) with an antigen-binding fragment specific for an astrocyte specific cell surface marker coupled to a solid surface, thereby labeling the cells expressing an astrocyte specific surface marker,
   d) isolating the non-labeled cells.
4. The method of claim 1 wherein the antigen-binding fragments are antibodies or antibody fragments.
5. The method of claim 1, wherein the solid phase is a magnetic particle.
6. The method of claim 2 wherein the antigen-binding fragment specific for an astrocyte specific cell surface marker is selected from the group consisting of Anti-ACSA-2 and Anti-GLAST (ACSA-1).
7. The method of claim 2 wherein the antigen-binding fragment specific for an astrocyte specific cell surface marker is ACSA-2.

* * * * *